United States Patent [19]

Thompson et al.

[11] Patent Number: 5,663,467
[45] Date of Patent: Sep. 2, 1997

[54] SYNTHESIS OF CYCLOPROPYLACETYLENE

[75] Inventors: Andrew S. Thompson, Mountainside; Edward G. Corley, Old Bridge; Martha Huntington, Edison, all of N.J.

[73] Assignee: Merck & Co., Inc., Rahway, N.J.

[21] Appl. No.: 376,611

[22] Filed: Jan. 23, 1995

[51] Int. Cl.$^6$ .................................................. C07C 1/207
[52] U.S. Cl. ............................................ 585/359; 585/534
[58] Field of Search ...................................... 585/359, 534

[56] References Cited

PUBLICATIONS

Militzer, et al., "Versatile Syntheses of Alkynyl- and Substituted Alkynylcyclopropanes: 2-Alkoxyethynylcyclopropanes . . . ", Synthesis, pp. 998–1000 (1972). No Month Available.

Schoberth, et al., "Eine einfache Herstellungsmethode fur Cyclopropylacetylen", Communications, Dec. 1972, p. 703, No Month Available.

Sherrod, et al., "Generation and Rearrangements of the 1-Cyclopropylvinyl Cation . . . ", Organic and Biological Chemistry, pp. 1925–1940, (1971), No Month Available.

Mikhailov, et al., "Synthesis of Polycyclic Compounds", J. of Gen. Chem. of the U.S.S.R., vol. XXII, pp. 195–201, No Month Available.

*Primary Examiner*—Glenn A. Caldarola
*Assistant Examiner*—Elizabeth D. Wood
*Attorney, Agent, or Firm*—Valerie J. Camara; Mark R. Daniel

[57] ABSTRACT

An improved synthesis of cyclopropylacetylene involving cyclization of 5-halo-1-pentyne in strong base is disclosed, and is useful for preparing compounds with a cyclopropylethynyl substituent, such as an intermediate for a highly potent HIV reverse transcriptase inhibitor or other pharmaceutically active compounds.

10 Claims, No Drawings

SYNTHESIS OF CYCLOPROPYLACETYLENE

BACKGROUND OF THE INVENTION

This case is related to U.S. Pat. No. 5,519,021 and allowed application Ser. No. 450,330 filed May 5, 1995.

A retrovirus designated human immunodeficiency virus (HIV) is the etiological agent of the complex disease that includes progressive destruction of the immune system (acquired immune deficiency syndrome; ADS) and degeneration of the central and peripheral nervous system. This virus was previously known as LAV, HTLV-III, or ARV. A common feature of retrovirus replication is reverse transcription of the RNA genome by a virally encoded reverse transcriptase to generate DNA copies of HIV sequences, a required step in viral replication. It is known that some compounds are reverse transcriptase inhibitors and are effective agents in the treatment of ADS and similar diseases, e.g., azidothymidine or AZT.

Nucleotide sequencing of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)].

Applicants demonstrate a substantially improved synthesis of an inhibitor of HIV reverse transcriptase, of the structure

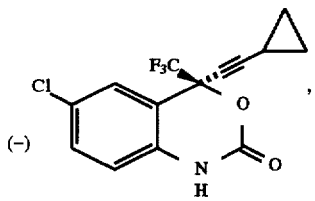

named (−)6-chloro-4-cyclopropylethynyl-4-trifluoromethyl-1,4-dihydro-2H-3,1-benzoxazin-2-one, hereinafter "Compound A." This compound is highly potent, even against HIV reverse transcriptase resistant to other AIDS antiviral compounds.

Applicants have devised a substantially improved synthesis of cyclopropylacetylene, an intermediate of Compound A. Prior methods employed two step procedures using corrosive reagents, and proceeded in low overall yield. See, for example, Militzer, H. C. et al., *Synthesis*, 998 (1993); Schoberth, W. et al., *Synthesis*, 703 (1972) [PCl$_5$ and base]; Sherrod, et al., *J. Am. Chem. Soc.*, 93:8, 1925–1940 (April, 1971) [I$_2$ on the hydrazone]; Mikhailov and Bronovitskaya, *Zh. Obshch. Khim.*, Vol. XXII, 195–201 (1952) [dibromide]. In contrast, the present process is shorter than prior methods, does not use corrosive reagents, and affords an overall yield as good or better than prior methods. The present process involves cyclization of 5-halo-1-pentyne in strong base.

Applicants have discovered that the successful outcome of this reaction requires generation of a transient dianion that cyclizes to cyclopropyl acetylene. No methods of the art generate a dianion. To the contrary, the art indicates that a variety of side reactions should occur, including chlorine displacement by the base or deprotonated acetylene, or halogen metal exchange of the chloride.

BRIEF DESCRIPTION OF THE INVENTION

An improved synthesis of cyclopropylacetylene is disclosed, an intermediate of Compound A. The synthesis involves cyclization of 5-halo-1-pentyne in strong base. Compound A is useful in the inhibition of HIV reverse transcriptase (and its resistant varieties), the prevention of infection by HIV, the treatment of infection by HIV and in the treatment of AIDS and/or ARC, either as compounds, pharmaceutically acceptable salts (when appropriate), pharmaceutical composition ingredients, whether or not in combination with other antivirals, anti-infectives, immunomodulators, antibiotics or vaccines. Methods of treating AIDS, methods of preventing infection by HIV, and methods of treating infection by HIV are also disclosed.

DETAILED DESCRIPTION OF THE INVENTION AND PREFERRED EMBODIMENTS

The process of the present invention is directed to preparing cyclopropylacetylene, a reagent useful for adding a cyopropylacetylene group to a wide variety of antivirals and other compounds of medicinal interest, especially inhibitors of HIV reverse transcriptase. In this invention, the process of preparing cyclopropylacetylene comprises the steps of (a) mixing at least about 1.0 equivalents of strong base in aprotic solvent with one equivalent of 5-halo-1-pentyne in aprotic solvent at a temperature of between about −20° and about 150° C.;

(b) allowing the temperature of the reaction mixture to rise to a range of between about 0° and about 150° C. and maintaining the temperature within the range for at least about 15 minutes, or until the cyclization is substantially complete; and (c) quenching the reaction with any proton source.

In one embodiment of the present invention, the process of preparing cyclopropylacetylene comprises the steps of (a) mixing at least about 1.0 equivalents of strong base in aprotic solvent with one equivalent of 5-halo-1-pentyne in aprotic solvent at a temperature of between about −20° and about 150° C.;

(b) allowing the temperature of the reaction mixture to rise to a range of between about 0° and about 150° C. and maintaining the temperature within the range for at least about 15 minutes, or until the cyclization is substantially complete;

(c) cooling the reaction mixture to a temperature of between about −30° and about 50° C.;

(d) quenching the reaction with any proton source.

In another embodiment of the present invention, there is added the final step of purifying the desired product cyclopropylacetylene.

One preferred embodiment of the present invention is a process of preparing cyclopropylacetylene, comprising the steps of (a) mixing between about 2.0 and about 2.5 equivalents of n-butyllithium in cyclohexane with one equivalent of 5-chloro-1-pentyne in cycyclohexane at about 0° C.;

(b) heating the reaction to about 75° C. and maintaining the reaction at that temperature for about 5 hours, or until the cyclization is substantially complete;

(c) cooling the reaction mixture to about 0° C.; and (d) quenching the reaction with saturated NH$_4$Cl; and, optionally, (e) purifying the desired product cyclopropylacetylene.

The process of the present invention is a one-pot process that begins with the mixing of one equivalent of 5-halo-1-pentyne in aprotic solvent with at least about 1.0 equivalents of strong base in aprotic solvent at a temperature of between about −20° and about 150° C. A preferred range of equivalents of strong base is between about 2.0 and about 2.5 equivalents. A preferred starting material is 5-chloro-1-pentyne. A preferred temperature for this mixing is within the range of between about −20° and about 25° C., most preferably at about 0° C. Before mixing, the aprotic solvent for the 5-halo-1-pentyne may or may not be the same as the aprotic solvent for the strong base.

The strong base is selected from the group consisting of n-butyl lithium, sodium amide, sodium diethyl amide, sodium hydride, potassium hydride, sodium bis(trimethylsilyl)amide, potassium bis(trimethylsilyl)amide, lithium diisopropylamide, sec-butyl lithium, tert-butyl lithium, and lithium tetramethyl piperidide. A preferred strong base is n-butyl lithium.

The aprotic solvent is selected from THF, 2,5-dimethyl THF, 1,4-dioxane, MTBE, diethoxymethane, dimethoxyethane, cyclohexane, hexane, and hexane with tetramethylene diamine. A preferred aprotic solvent is cyclohexane.

The mixing of strong base and 5-halo-1-pentyne is an exothermic reaction resulting in cyclization. Cyclization occurs spontaneously. It is preferred to heat the reaction sufficiently to accelerate cyclization. A preferred temperature for cyclization is within the range of between about 50° and about 80° C., preferably about 75° C. The higher the temperature, the shorter the incubation time needed to substantially complete cyclization. For the temperature of 75° C., an incubation time of about 5 hours is typically needed to complete cyclization. It will be understood that variations of temperature and incubation time in this cyclization step are readily determined by a skilled artisan.

When cyclization is substantially complete, or at least sufficiently complete, one may optionally cool the reaction mixture to a temperature of between about −30° and about 50° C., preferably a temperature of about 0° C.

Thereafter, a proton source is added to quench the reaction. In this invention, the proton source is selected from saturated NH$_4$Cl, HCl, and H$_2$SO$_4$. A preferred proton source is NH$_4$Cl.

Finally, a purification step for isolating cyclopropylacetylene may be included at this point.

The reactions used for adding cyclopropylacetylene groups onto cores of other molecules involves generally known chemistry and are well within the skill of the art. For adding the cyclopropylacetylene group to aromatic subtituents, a palladium-catalyzed coupling is readily performed. A displacement reaction is carried out for adding cyclopropylacetylene group to alkyl substituents.

The compounds of the present invention may have asymmetric centers and may occur, except when specifically noted, as racemates, racemic mixtures or as individual diastereomers, or enantiomers, with all isomeric forms being included in the present invention. The term (+/−) is intended to encompass (+) optical isomers or (−) optical isomers or mixtures thereof.

When any variable (e.g., R, aprotic solvent) occurs more than one time in any step, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms. "Halogen" or "halo" as used herein, means fluoro, chloro, bromo and iodo.

In this invention, cyclopropylacetylene is prepared by the following Scheme.

SCHEME I

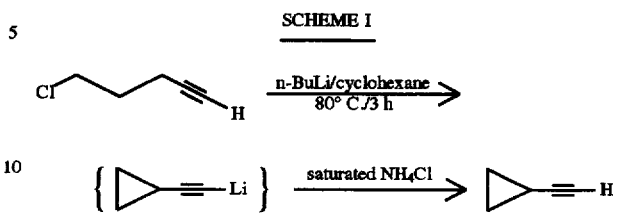

The overall yield is above 65%. In contrast, a prior method using corrosive reagents gave about 42% yield, and is set forth as follows:

SCHEME II

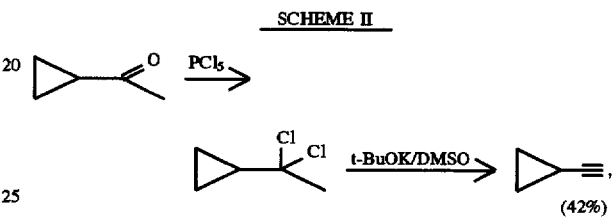

as also described in L. E. Hudson et al., *J. Am. Chem. Soc.*, 94, 1158 (1972) and W. Schoberth et al., *Synthesis*, 703 (1972).

Compound A can be synthesized by the following method.

SCHEME III

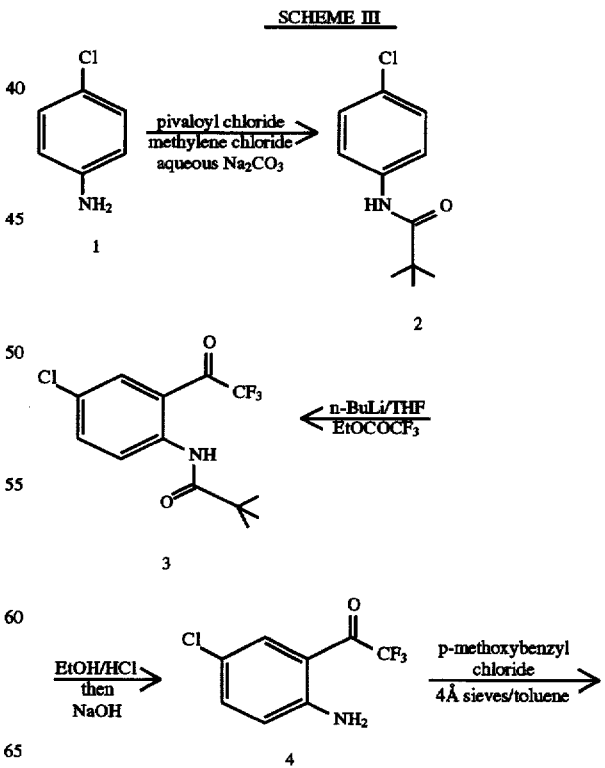

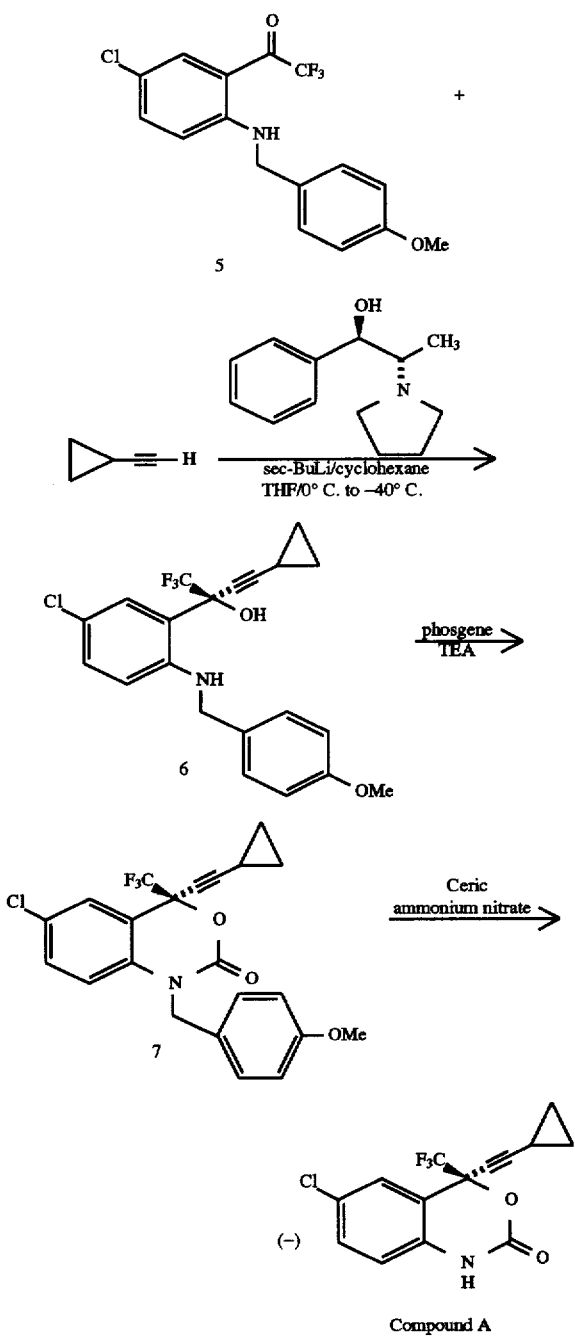

-continued
SCHEME III

Compound A

Compound A is useful in the preparation and execution of screening assays for antiviral compounds: For example, Compound A is useful for isolating enzyme mutants, which are excellent screening tools for more powerful antiviral compounds. Furthermore, Compound A is useful in establishing or determining the binding site of other antivirals to HIV reverse transcriptase, e.g., by competitive inhibition. Thus Compound A is a commercial product to be sold for these purposes.

Compound A is useful in the inhibition of HIV reverse transcriptase, the prevention or treatment of infection by human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the compound of this invention is useful in treating infection by HIV after suspected past exposure to HIV by e.g., blood transfusion, exchange of body fluids, bites, accidental needle stick, or exposure to patient blood during surgery.

The particular advantage of Compound A is its potent inhibition against HIV reverse transcriptase rendered resistant to other antivirals, such as L-697,661, which is 3-([(4, 7-dichloro-1,3-benzoxazol-2-yl)methyl]-amino)-5-ethyl-6-methyl-pyridin-2(1H)-one; or L-696,229, which is 3-[2-(1, 3-benzoxazol-2-yl)ethyl]-5-ethyl-6-methyl-pyridin-2(1H)-one; or AZT.

For these purposes, Compound A may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention there is further provided a method of treating and a pharmaceutical composition for treating HIV infection and AIDS. The treatment involves administering to a patient in need of such treatment a pharmaceutical composition comprising a pharmaceutical carrier and a therapeutically-effective amount of a compound of the present invention.

These pharmaceutical compositions may be in the form of orally-administrable suspensions or tablets; nasal sprays; sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweeteners/flavoring agents known in the art. As mediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these compositions may be prepared by mixing the drug with a suitable non-irritating excipient, such as cocoa butter, synthetic glyceride esters or polyethylene glycols, which are solid at ordinary temperatures, but liquidify and/or dissolve in the rectal cavity to release the drug.

Compound A can be administered orally to humans in a dosage range of 1 to 100 mg/kg body weight in divided doses. One preferred dosage range is 0.1 to 10 mg/kg body weight orally in divided doses. Another preferred dosage range is 0.1 to 20 mg/kg body weight orally in divided doses. For combination therapy with nucleoside analogs, a preferred dosage range is 0.1 to 20 mg/kg body weight for the compounds of this invention administered orally in divided doses, and 50 mg to 5 g/kg body weight for nucleoside analogs administered orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drag combination, the severity of the particular condition, and the host undergoing therapy.

EXAMPLE 1

Preparation of Cyclopropylacetylene

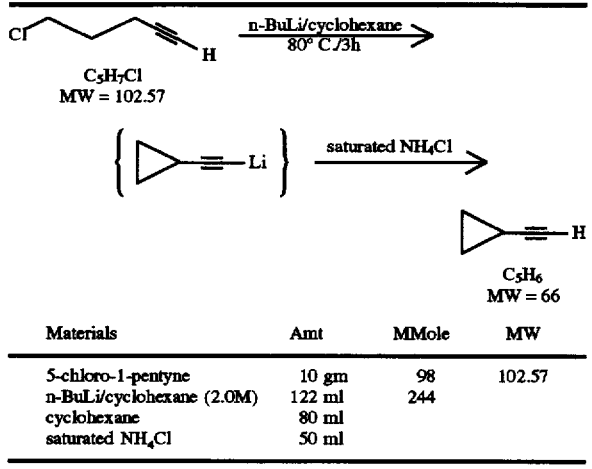

| Materials | Amt | MMole | MW |
|---|---|---|---|
| 5-chloro-1-pentyne | 10 gm | 98 | 102.57 |
| n-BuLi/cyclohexane (2.0M) | 122 ml | 244 | |
| cyclohexane | 80 ml | | |
| saturated NH$_4$Cl | 50 ml | | |

To a solution of 5-chloro-1-pentyne in cyclohexane (80 ml) at 0° C. under N$_2$ was added n-butyllithium in cyclohexane (2.0M, 122 ml). The mixture was heated to 75° C. for 5 h.

Addition of n-butyllithium to the alkyne was exothermic, the temperature was maintained below +5° C. during these additions using an ice-H$_2$O bath.

The progress of the cyclization step was monitored by HPLC. The reaction was considered complete when the assay yield was >90%.

HPLC conditions: Phenyl column, CH$_3$CN, water, phosphoric acid; 50:50:0.1 isocratic elution for 20 minutes, flow=1.0 ml/min, UV detection at 195 nm, starting material t$_R$=7.5 min, cylopropylacetylene t$_R$=6.0 min. The product has a response factor which was 20 times greater than the starting material.

Once the cyclization step was complete, the reaction was cooled to 0° C. and quenched with saturated NH$_4$Cl.

Assay of the organic phase by HPLC showed 5.5 gm of cyclopropylacetylene (85% yield).

The product was purified by fractional distillation through a 6"×0.5" column packed with 4 mm glass beads. The fraction with a boiling point between 45°–75° C. was collected.

This afforded 4.2 gm (65%) of cyclopropylacetylene as a colorless oil.

EXAMPLE 2

Preparation of 4-Chlorophenyl-pivalamide

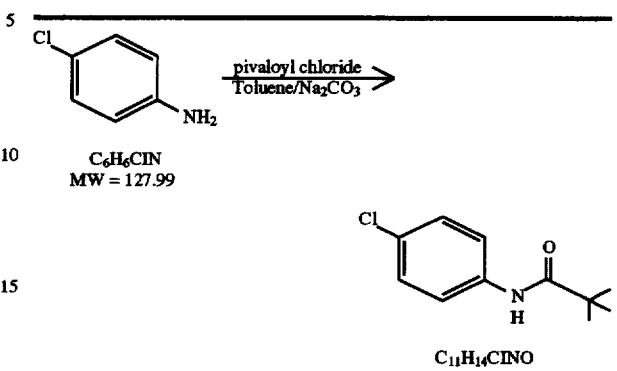

| Materials | Amt | MMole | MW |
|---|---|---|---|
| 4-chloroaniline | 76 gm | 596 | 127.57 |
| Pivaloyl chloride (d = 0.979) | 74 ml | 600 | 120.58 |
| toluene | 600 ml | | |
| saturated Na$_2$CO$_3$ | 95 ml | | |
| D.I. water | 225 ml | | |

To a solution of 4-chloroaniline (76 gm) in toluene (600 ml) was added saturated Na$_2$CO$_3$ (95 ml). The batch was cooled to 10° C. and pivaloyl chloride (74 ml) was added dropwise over 45 minutes. The batch was stirred at 5°–10° C. for 60 minutes while the progress of the reaction was monitored by HPLC.

Addition of pivaloyl chloride to the aniline was exothermic. HPLC conditions: C-8 column, CH$_3$CN, water, phosphoric acid; gradient elution from 40:60:0.1 to 80:20 0.1 over 20 minutes, flow=1.0 ml/min, UV detection at 245 nm, starting material t$_R$=7.2 min, pivalamide t$_R$=12.6 min.

The product was isolated by filtration and washed with D.I. water (3×75 ml) and air dried under suction for 10 minutes. The product was dried in a vacuum oven at 40° C. with an N$_2$ purge for 16 h to afford 108.5 gm of product as fine whim needles (86%).

EXAMPLE 3

Preparation of 4-Chloro-keto-aniline

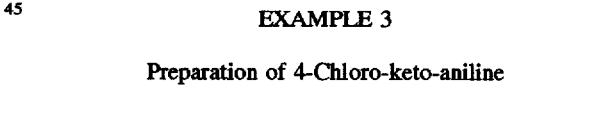

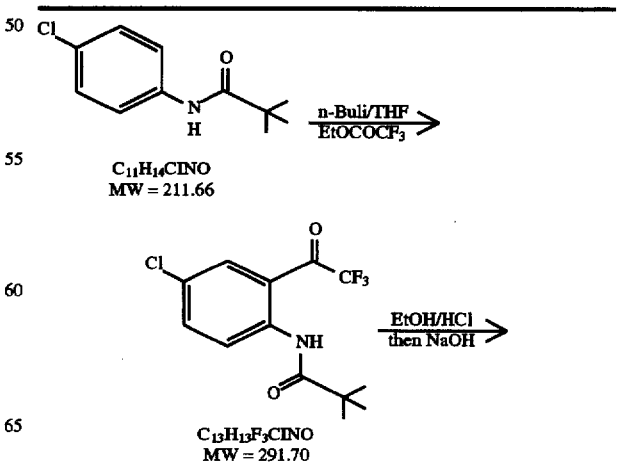

-continued

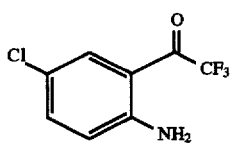

C₈H₅F₃ClNO
MW = 223.58

| Materials | Amt | MMole | MW |
|---|---|---|---|
| 4-chlorophenyl pivalamide | 10 gm | 47.2 | 211.69 |
| n-BuLi/hexane (2.5M) | 38 ml | 95 | |
| ethyl trifluoroacetate (d = 1.194) | 6.7 ml | 56.6 | 142.08 |
| THF | 75 ml | | |
| Ethanol | 90 ml | | |
| 6N HCl | 50 ml | 240 | |
| hexane | 90 ml | | |
| 2N NaOH | 15 ml | | |
| D.I. water | 350 ml | | |

In a 500 ml 3 necked flask the pivalamide (10 gm) was dissolved in dry THF (75 ml) and the mixture was cooled to 0° C. To this solution was added n-BuLi/hexane (2.5M, 38 ml) dropwise while allowing the internal temperature to rise to +15° C. The batch was aged at 0° C. for 2 h.

Addition of the first equivalent of n-BuLi to the pivalamide was highly exothermic. The exotherm was controlled by the rate of addition.

To the resulting light yellow suspension was added neat ethyl trifluoroacetate (6.7 ml), while allowing the internal temperature to rise to 10° C. The progress of the reaction was monitored by HPLC.

HPLC conditions: C-8 column, $CH_3CN$, water, phosphoric acid; gradient elution from 40:60:0.1 to 80:20 0.1 over 20 minutes, flow=1.0 ml/min, UV detection at 245 nm, starting pivalamide $t_R$=12.6 min, keto-pivalamide $t_R$=11.6 min. There was typically 85A % product and 10–15A % unreacted pivalamide.

The reaction was quenched by adding 6N HCl (10 ml) and D.I. water (20 ml).

HPLC assay at this point showed 13.1 gm (90%) of product.

The solution was concentrated to ca. 50 ml in vacuo, and flushed with ethanol (50 ml) to remove hexane and THF. To the batch was added 6N HCl (40 ml) and the mixture was heated to reflux (80° C.) for 1 h.

HPLC assay shows 85–90A % of the keto-aniline, 10A % unreacted pivalamide. Thus the acylated material undergoes hydrolysis while unreacted pivalamide remains unchanged. The assay yield at this point was 7.78 gm (74%).

The batch was concentrated to ca. 50 ml in vacuo, at which time a precipitate formed (presumably the HCl salt of the product). The distillation was discontinued and the batch was cooled to 0° C. After a 1 h age, the batch was filtered and washed with hexane (3×30 ml).

The hexane washes remove unreacted pivalamide from the product. The solid is checked by HPLC to ensure it has been completely removed at this point. The filtrate and washes typically contain 1.2–1.5 gm of product (8–12%). The majority of product loss was in the aqueous filtrate.

The salt was dried in a vacuum oven at 40° C. for 16 h to afford 10.4 gm of a solid which was 71.4% pure by weight (70% yield). The salt was slurried in D.I. water (260 ml) and neutralized to a pH of ca. 6–7 with 2N NaOH (15 ml).

It was critical not to bring the pH above 9.0 due to product decomposition.

The resulting bright yellow solid was isolated by filtration and washed with D.I. water (2×25 ml). The product was dried in a vacuum oven at 40° C. for 16 h to afford 6 gm of keto aniline which was 96.6% pure by weight (54% yield).

The product is further purified by recrystallization from hexane.

EXAMPLE 4

Preparation of N-4-methoxybenzyl-keto-aniline

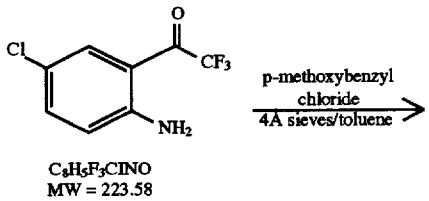

C₈H₅F₃ClNO
MW = 223.58

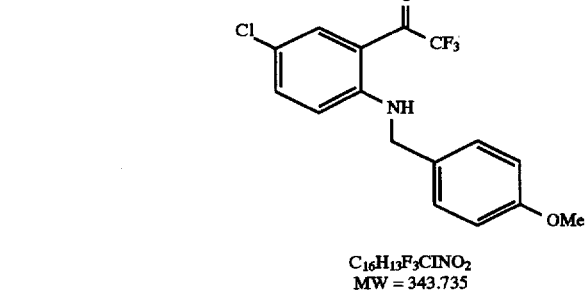

C₁₆H₁₃F₃ClNO₂
MW = 343.735

| Materials | Amt | MMole | MW |
|---|---|---|---|
| keto-aniline | 15.5 gm | 69.5 | 223.58 |
| p-methoxy-benzylchloride | 10.9 gm | 69.8 | |
| 4Å molecular sieves | 90 gm | | |
| Toluene | 70 ml | | |
| Acetone | 500 ml | | |
| Hexane | 120 ml | | |

In a 250 ml flask was charged the keto-aniline (15.5 gm), activated 4 Å molecular sieves (50 gm) and toluene (75 ml). The mixture was stirred at 23° C. under $N_2$ for 24 h. Assay by HPLC showed ca. a 1:1 mixture of product and starting material.

HPLC conditions: C-8 column, $CH_3CN$, water, phosphoric acid; isocratic elution at 65:35:0.1 over 20 minutes, flow=1.0 ml/min, UV detection at 260 nm, toluene $t_R$=5.7 min, starting keto-aniline $t_R$=6.5 min, product $t_R$=15.0 min. There was typically 25A % of toluene. The reaction was charged with fresh molecular sieves (40 gm) and stirred for an additional 3 days at 23° C. The reaction was judged complete when less than 2A % of starting material remained.

The mixture was filtered through celite and washed with acetone (7×75 ml) until most of the yellow color was washed from the celite. The filtrate was concentrated to afford 27 gm of a yellow-orange oil which solidified on standing. The solid was purified by dissolving it in hot hexanes (100 ml). The batch was cooled to rt, then to 0° C. in an ice-$H_2O$ bath. After a 1.5 h age, the batch was filtered and washed with cold hexanes (2×10 ml). The batch was air dried with suction for 10 minutes, then dried in a vacuum oven at 40° C. for 2 h. This afforded 20.5 gm (86%) of a bright yellow powder.

EXAMPLE 5

Preparation of the Amino Alcohol

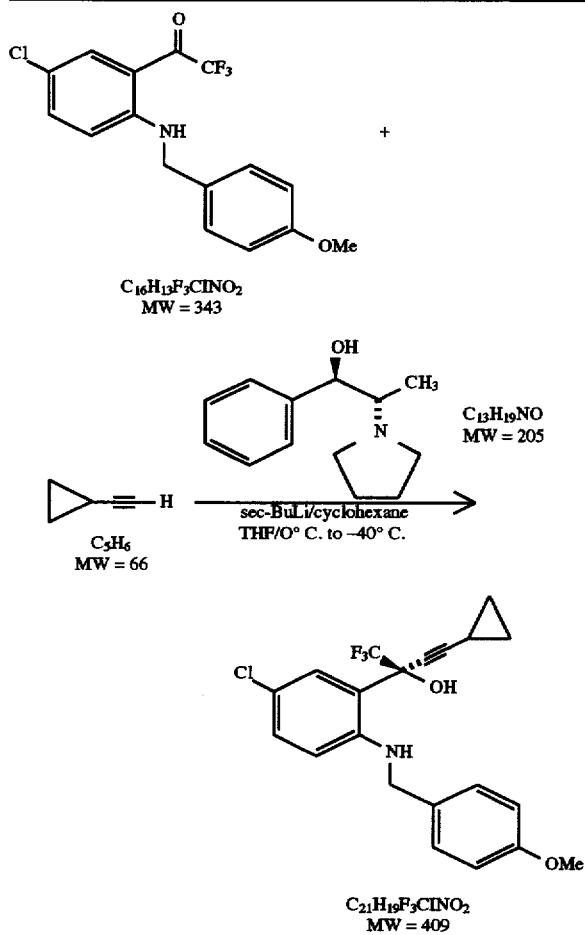

| Materials | Amt | mmol | MW |
|---|---|---|---|
| Ketone | 175 mg | 0.51 | 343 |
| 1R, 2S N-pyrrolidinyl norephedrine | 264 mg | 1.3 | 205 |
| cyclopropyl acetylene (d = 0.8) | 0.1 ml | 1.21 | 66 |
| sec-BuLi (1.3M in cylohexane) | 2 ml | 2.6 | |
| THF (KF = 20 µg/ml) | 4 ml | | |
| 1M Citric acid | 10 ml | | |
| Ethyl acetate | 6 ml | | |

The pyrrolidinyl ephedrine (264 mg) was dissolved in THF (2 ml) and the mixture was cooled to −5° C. To the mixture at −5° C. under $N_2$ was added neat cyclopropylacetylene (0.11 ml) and sec-butyllithium (2.0 ml) dropwise. The mixture was aged at −5° C. for 30 minutes, then cooled to −45° C.

The addition of sec-butyllithium caused an exotherm which was maintained between −5° to 0° C. by the rate of addition.

The ketone (175 mg) was dissolved in THF (1.0 ml) under $N_2$ and added to the anionic mixture over 2–3 minutes allowing the internal temperature to rise to −40° C. during the addition. The resulting light orange solution was aged at −40° C. for 60 minutes and quenched by adding 1M citric acid (3 ml) and ethyl acetate (3 ml). The reaction was warmed to ambient temperature and the layers were separated. The lower water layer was extracted with ethyl acetate (3 ml). The combined organic layers were washed with 1M citric acid (2×3 ml). The reaction mixture was assayed by HPLC for percent conversion and product EE.

HPLC conditions: C-8 column, $CH_3CN$:water:phosphoric acid, isocratic elution 65:35:0.1 for 20 minutes, flow=1.0 ml/min, UV detection at 252 nm, st. material $t_R$=12.8 min, product $t_R$=10.3 min.

Chiral HPLC conditions: amylose stationary phase column, hexane:isopropanol 85:15 isocratic elution, flow= 1.0 ml/min, UV detection at 252 nm, st. material $t_R$=4.9 min, major enantiomer $t_R$=5.5 min, minor enantiomer $t_R$=25.0 min.

The enantiomeric excess was 98% and the reaction conversion was 93%. (6A % starting material). The assay yield was 92%.

EXAMPLE 6

Preparation of the Benzoxazinone

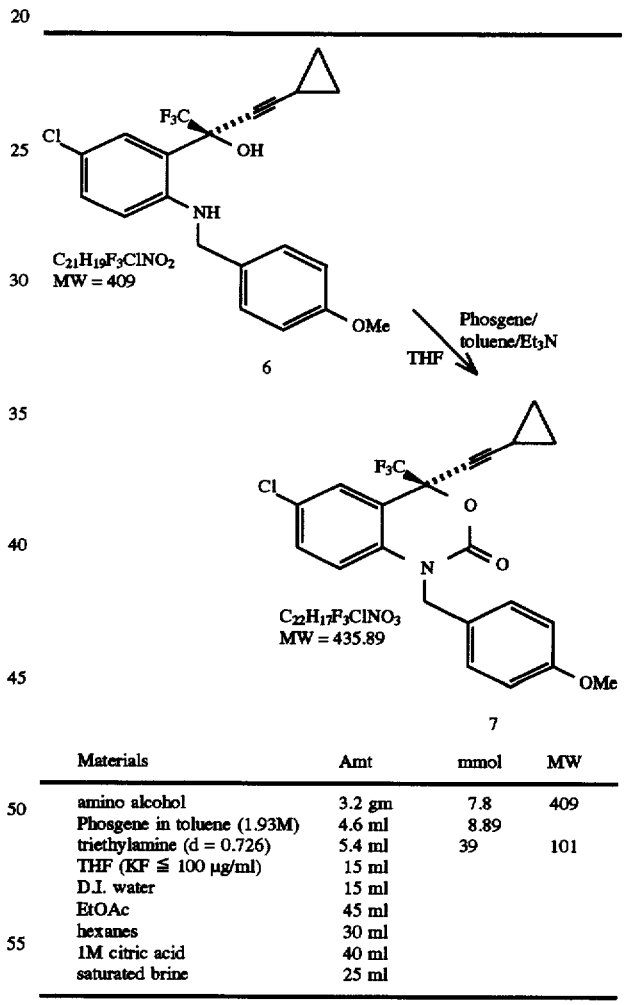

| Materials | Amt | mmol | MW |
|---|---|---|---|
| amino alcohol | 3.2 gm | 7.8 | 409 |
| Phosgene in toluene (1.93M) | 4.6 ml | 8.89 | |
| triethylamine (d = 0.726) | 5.4 ml | 39 | 101 |
| THF (KF ≦ 100 µg/ml) | 15 ml | | |
| D.I. water | 15 ml | | |
| EtOAc | 45 ml | | |
| hexanes | 30 ml | | |
| 1M citric acid | 40 ml | | |
| saturated brine | 25 ml | | |

The amino-alcohol was dissolved in THF (15 ml) and cooled to −10° C. under $N_2$. To the mixture was added triethylamine (5.4 ml) and phosgene in toluene (4.6 ml). The addition of phosgene caused an exotherm which was maintained below 20° C. by the rate of addition. The progress of the reaction was monitored by HPLC and was typically complete in 15 minutes.

HPLC conditions: C-8 column, $CH_3CN$:water:phosphoric acid, gradient elution from 50:50:0.1 to 90:10:0.1 over 20 minutes, flow=1.5 ml/min, UV detection at 252 nm. st. material $t_R$=4.6 min, product $t_R$=16.0 min.

The reaction was cooled to 0° C. and quenched with ice-cold water (15 ml) and ethyl acetate (20 ml). Saturated brine was used to break-up any emulsions. The organic layer was removed and the aqueous was extracted with ethyl acetate (15 ml). The combined organics were washed with 1M citric acid (40 ml) and saturated brine (25 ml). The organic was dried ($Na_2SO_4$) and concentrated in vacuo to afford 3.8 gm of a brown oil.

The product was crystallized from 5:1 hexane:ethyl acetate (25 ml), chilled to 0° C., aged for 1 h and filtered. The cake was washed with cold 5:1 hexane:ethyl acetate (2×5 ml). The cake was air dried with suction to afford 2.9 gm (85%) of a light orange solid.

EXAMPLE 7

Preparation of Compound A

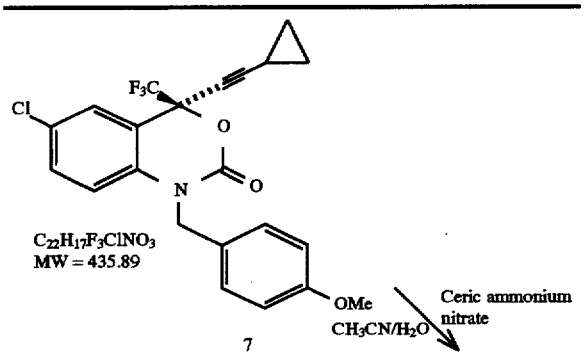

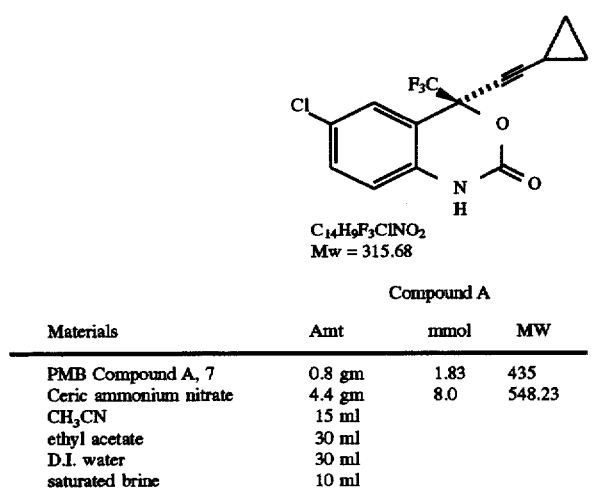

Compound A

| Materials | Amt | mmol | MW |
|---|---|---|---|
| PMB Compound A, 7 | 0.8 gm | 1.83 | 435 |
| Ceric ammonium nitrate | 4.4 gm | 8.0 | 548.23 |
| $CH_3CN$ | 15 ml | | |
| ethyl acetate | 30 ml | | |
| D.I. water | 30 ml | | |
| saturated brine | 10 ml | | |

The p-methoxybenzyl protected Compound A was dissolved in $CH_3CN$ (15 ml). To this solution was added a solution of ceric ammonium nitrate (4.4 gm) in water (5 ml). The reaction was typically complete in 2 h at 23° C. as determined by HPLC.

HPLC conditions: C-8 column, $CH_3CN$:water:phosphoric acid, gradient elution from 50:50:0.1 to 90:10:0.1 over 20 minutes, flow=1.5 ml/min, UV detection at 252 nm, st. material $t_R$=16.0 min, product $t_R$=9.0 min.

The reaction was diluted with D.I. water (5 ml) and concentrated to ca. ½ volume. The product was extracted from the resulting aqueous layer with ethyl acetate (2×15 ml). The combined organic was washed with D.I. water (2×10 ml) and brine (10 ml). The organic was concentrated in vacuo to afford a yellow gum. The product was isolated by silica gel chromatography.

EXAMPLE 8

N-(4-chlorophenyl)-2,2-dimethylpropanamide

To a 5 L 3 necked round bottomed flask with an overhead stirrer was added 4-chloroaniline (127.57 g, 1 mole), 1200 mL of $CHCl_3$, and 1200 mL of saturated aqueous $Na_2CO_3$ solution. An addition funnel was attached to the flask and charged with 2,2-dimethylpropanoyl chloride (129 mL, 1.05 mole). The acid chloride was added dropwise to the vigorously stirred mixture over 1 h. The resulting mixture was stirred at ambient temperature for an additional 23 h. Some of the product separated from the mixture as white crystals. These crystals were collected by filtration. The filtrate was transferred to a separatory funnel and the layers were separated. The chloroform layer was washed with water and brine. Drying ($MgSO_4$), filtration, and removal of the solvent in vacuo gave additional product. The two portions of product were combined and recrystallized from boiling EtOAc-hexanes to give 185.6 g of N-(4-chlorophenyl)-2,2-dimethylpropanamide as a white crystalline solid.

EXAMPLE 9

(−)6-Chloro-4-cyclopropylethynyl-4-trifluoromethyl-1,4-dihydro-2H-3,1-benzoxazin-2-one (Compound A) and (+)6-Chloro-4-cyclopropylethynyl-4-trifluoromethyl-1,4-dihydro-2H-3,1-benzoxazin-2-one Step A: 2-(2-Amino-5-chlorophenyl)-4-cyclopropyl-1,1,1-trifluoro-3-butyn-2-ol A solution of bromomagnesium cyclopropylacetylide, was prepared from 23 g of cyclopropylacetylene (0.348 mol) in 250 mL of THF by dropwise addition of 116 mL of a 3.0M solution of ethylmagnesium bromide in ether (0.348 mol) over 1 h. This solution was maintained at 0° C. for 1 h, then at 40° C. for 3 h. To this solution, recooled to 0° C., 15.56 g of 1-(2-amino-5-chlorophenyl)-2,2,2-trifluoromethylethanone (0.0696 mol), was added as a solid, portionwise over 5 min. The reaction mixture was allowed to stir at 0° for 1.5 hours. The reaction was quenched at 0° C. by dropwise addition of 700 mL of saturated aqueous ammonium chloride solution. The mixture was extracted with 2×400 mL portions of ethyl acetate, the combined organic phases were washed with brine and dried over $MgSO_4$. Removal of the drying agent and solvents left a yellow solid. This material was recrystallized from boiling hexanes (100 mL final volume) to afford 14.67 g of 2-(2-amino-5-chlorophenyl)-4-cyclopropyl-1,1,1-trifluoro-3-butyn-2-ol. A second crop (2.1 g) was obtained from concentrating the mother liquors. mp: 153°–154° C. $^1$H-NMR ($CDCl_3$): δ0.84 (m, 2H), 0.90 (m, 2H), 1.38 (m, 1H), 4.50 (br s, 3H), 6.69 (d, J=8.5 Hz, 1H), 7.13 (dd, J=2.5, 8.5 Hz, 1H), 7.55 (d, J=2.5 Hz, 1H).

Step B: (±)6-Chloro-4-cyclopropylethynyl-4-trifluoromethyl-1,4-dihydro-2H-3,1-benzoxazin-2-one A solution of 2-(2-amino-5-chlorophenyl)-4-cyclopropyl-1,1,1-trifluoro-3-butyn-2-ol (15.00 g, 0.0518 mol) and 41.98 g (0.259 mol) of 1,1'-carbonyldiimidazole in 250 mL of dry THF was stirred under argon at 55° C. for 24 hours. The solvent was removed on a rotary evaporator and the residue was partitioned between 500 mL of ethyl acetate and 400 mL of water. The layers were separated and the aqueous phase was extracted once more with ethyl acetate. The combined ethyl acetate extracts were washed with 2×200 mL of 2% aqueous HCl, saturated aqueous NaHCO$_3$, and brine. Drying over MgSO$_4$, filtration, and removal of the solvent in vacuo provided 16.42 g of the title compound as a solid. Recrystallization from ethyl acetate-hexane afforded 12.97 g of analytically pure (±)6-chloro-4-cyclo-propylethynyl-4-trifluoromethyl-1,4-dihydro-2H-3,1-benzoxazin-2-one as a white crystals. mp: 178°–180° C. $^1$H-NMR (CDCl$_3$): 0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d, J=2.5 Hz, 1H), 8.87 (br s, 1H).

Step C: 6-Chloro-1-(1S)-camphanoyl-4-cyclopropylethynyl-4-trifluoromethyl-1,4-dihydro-2H-3,1-benzoxazin-2-one To a solution containing (±)6-chloro-4-cyclopropylethynyl-4-trifluoromethyl-1,4-dihydro-2H-3,1-benzoxazin-2-one (12.97 g, 0.041 mol), 4-dimethylaminopyridine (1.02 g, 0.0083 mol), and (−) camphanic acid chloride (14.22 g, 0.06556 mol) in 350 mL of dry dichloromethane, stirred under argon in an ice bath, was added triethyl-amine (22.84 mL, 0.164 mol). The cooling bath was removed and the reaction was allowed to proceed at room temperature. After 75 min the reaction was judged complete by thin layer chromatography (SiO$_2$, 4% EtOAc in CHCl$_3$), and the solution was diluted with 500 mL of CHCl$_3$ then washed with 10% citric acid (2×), water (1×), and brine (1×). Drying (MgSO$_4$), filtration, and removal of the solvent in vacuo left a colorless foam. This material was triturated with 200 mL of boiling hexane. On cooling to room temperature the desired diastereomeric camphanate imide precipitated. The solid was collected on a frit, washed with a little cold hexanes and dried in vacuo to give 7.79 g of 6-chloro-1-(1S)-camphanoyl-4-cyclo-propylethynyl-4-trifluoromethyl-1,4-dihydro-2H-3,1-benzoxazin-2-one as white crystals. mp: 164°–165° C. HPLC purity: 99.2% @254 nm. $^1$H-NMR (CDCl$_3$): δ0.77 (s, 3H), 0.86–0.96 (m, 4H), 1.08 (s, 3H), 1.19 (s, 3H), 1.44 (m, 1H), 1.76 (m, 1H), 1.95 (m, 1H), 2.51 (m, 2H), 7.42 (dd, J=2.4, 9.0 Hz, 1H), 7.63 (m, 2H).

Step D: (−) 6-Chloro-4-cyclopropylethynyl-4-trifluoromethyl-1,4-dihydro-2H-3,1-benzoxazin-2-one (Compound A)

6-Chloro-1-(1S)-camphanoyl-4-cyclopropylethynyl-4-trifluoromethyl-1,2-dihydro-4(H)-3,1-benzoxazin-2-one (7.50 g, 0.01512 mol) was dissolved in 150 mL of n-butanol at 60° C. under an atmosphere of argon. To this solution was added 10 mL of 1N HCl. This solution was maintained at 60° C. for 72 h. The mixture was neutralized with aqueous NaHCO$_3$ and the n-butanol was removed in vacuo. The residue was dissolved in 150 mL of THF and treated with 50 mL of 2N LiOH for 3 h at room temperature. This mixture was diluted with ethyl acetate and washed with two portions of water and one of brine. Drying (MgSO$_4$), filtration and removal of the solvent in vacuo gave a white solid. This material was recrystallized from hot hexane to give 3.43 g of (−) 6-chloro-4-cyclopropylethynyl-4-trifluoromethyl-1,4-dihydro-2H-3,1 -benzoxazin-2-one as white crystals. mp: 131°–132° C.; [α]$_D^{20}$=−84.7° (CHCl$_3$, c=0.005 g mL$^{-1}$); $^1$H-NMR (CDCl$_3$): δ0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d, J=2.5 Hz, 1H), 8.87 (br s, 1H).

Step E: (+)6-Chloro-4-cyclopropylethynyl-4-trifluoromethyl-1,4-dihydro-2H-3,1-benzoxazin-2-one The mother liquors from Step C above were purified by column chromatography on silica gel using 10% ethyl acetate in hexanes as eluant. The pure, undesired diastereomer (a colorless foam) was hydroylzed according to Step D. The enantiomeric benzoxazinone, (+)6-chloro-4-cyclopropylethynyl-4-trifluoromethyl-1,4-dihydro-2H-3,1-benzoxazin-2-one, was obtained as white crystals. mp: 131°–132° C.; [α]$_D^{20}$=+84.4° (CHCl$_3$, c=0.005 g mL$^{-1}$); $^1$H-NMR (CDCl$_3$): δ0.85 (m, 2H), 0.94 (m, 2H), 1.40 (m, 1H), 6.81 (d, J=8.5 Hz, 1H), 7.37 (dd, J=2.5, 8.5 Hz, 1H), 7.49 (d, J=2.5 Hz, 1H), 8.87 (br s, 1H).

REVERSE TRANSCRIPTASE ASSAY

The assay measures the incorporation of tritiated deoxyguanosine monophosphate by recombinant HIV reverse transcriptase (HIV RT$_R$) (or other RT) into acid-precipitable cDNA at the Km values of dGTP and poly r(C).oligo d(G)$_{12-18}$. The inhibitors of the present invention inhibit this incorporation.

The assays were carried out in 55 mM Tris (pH 8.2)—30 mM KCl—30 mM MgCl$_2$—1 mM dithiothreitol—20 µg of rC:dG$_{12-18}$ (Pharmacia) per ml—8 mM [$^3$H]dGTP (New England Nuclear)—0.01% Triton X-100—50 mM ethylene glycol-bis(β-amino-ethyl ether)-N,N,N',N'-tetraacetic acid (EGTA)—1 mg of bovine serum albumin per ml. After 60 min of incubation at 37° C., acid-precipitable material was collected onto glass fiber filters by using a semiautomatic cell harvester. Bacterial cell extracts containing RT were diluted to within the linear range of the assay, and activity was determined in the presence and absence of inhibitor. Purified HIV-1 RT heterodimer produced in *E. coli* also served as a control. Results are determined as inhibitor concentration to give 50% inhibition (IC$_{50}$ wt), in nanomoles/liter. Compound A gave an IC$_{50}$ wt of 2 nM.

For the double mutant assay (dm), A17 RT was employed in the assay. A17 RT is resistant to various aminopyridones, as described in Nunberg, J. H. et al., *J. Virol.*, 65, 4887 (1991). Results are measured as IC$_{50}$ dm in nanomoles/liter. Compound A gave an IC$_{50}$ wt of 85 nM.

CELL SPREAD ASSAY

Inhibition of the spread of HIV in cell culture was measured according to Nunberg, J. H. et al., *J. Virol.*, 65, 4887 (1991). In this assay, MT-4 T-lymphoid cells were infected with HIV-1 (wild-type, unless otherwise indicated) by using a predetermined inoculum, and cultures were incubated for 24 h. At this time, ≦1% of the cells were positive by indirect immunofluorescence. Cells were then extensively washed and distributed into 96-well culture dishes. Serial twofold dilutions of inhibitor were added to the wells, and cultures were continued for 3 additional days. At 4 days postinfection, 100% of the cells in control cultures were infected. HIV-1 p24 accumulation was directly correlated with virus spread. The cell culture inhibitory concentration was defined as the inhibitor concentration in nanomoles/liter which reduced the spread of infection by at least 95%, or CIC$_{95}$.

While the foregoing specification teaches the principles of the present invention, with examples provided for the purpose of illustration, it will be understood that the practice of the invention encompasses all of the usual variations, adaptions, or modifications, as come within the scope of the following claims and its equivalents.

What is claimed is:

1. A process of preparing cyclopropylacetylene, comprising the steps of
   (a) mixing at least about 1.0 equivalents of strong base chosen from the group consisting of n-butyl lithium, sodium amide, sodium diethyl amide, sodium hydride, potassium hydride, sodium bis(trimethylsilyl)amide, potassium bis(trimethylsilyl)amide, lithium diisopropylamide, sec-butyl lithium, tert-butyl lithium, and lithium tetramethyl piperidide in aprotic solvent with one equivalent of 5-halo-1-pentyne in aprotic solvent at a temperature of between about −20° and about 150° C.;
   (b) allowing the temperature of the reaction mixture to rise to a range of between about 0° and about 150° C. and maintaining the temperature within the range for at least about 15 minutes, or until the cyclization is substantially complete; and
   (c) quenching the reaction with any proton source.

2. A process of preparing cyclopropylacetylene, comprising the steps of
   (a) mixing at least about 1.0 equivalents of strong base chosen from the group consisting of n-butyl lithium, sodium amide, sodium diethyl amide, sodium hydride, potassium hydride, sodium bis(trimethylsilyl)amide, potassium bis(trimethylsilyl)amide, lithium diisopropylamide, sec-butyl lithium, tert-butyl lithium, and lithium tetramethyl piperidide in aprotic solvent with one equivalent of 5-halo-1-pentyne in aprotic solvent at a temperature of between about −20° and about 150° C.;
   (b) allowing the temperature of the reaction mixture to rise to a range of between about 0° and about 150° C. and maintaining the temperature within the range for at least about 15 minutes, or until the cyclization is substantially complete;
   (c) cooling the reaction mixture to a temperature of between about −30° and about 50° C.;
   (d) quenching the reaction with any proton source.

3. The process of claim 2 further comprising purifying the desired product cyclopropylacetylene.

4. The process of claim 1, wherein the strong base is n-butyl lithium.

5. The process of any of claims 1–3, wherein the aprotic solvent is selected from THF, 2,5-dimethyl THF, 1,4-dioxane, MTBE, diethoxymethane, dimethoxyethane, cyclohexane, hexane, and hexane with tetramethylene diamine.

6. The process of claim 5, wherein the aprotic solvent is cyclohexane.

7. The process of any of claims 1–3, wherein the proton source is selected from saturated $NH_4Cl$, HCl, and $H_2SO_4$.

8. The process of any of claims 1–3, wherein 5-halo-1-pentyne is 5-chloro-1-pentyne.

9. A process of preparing cyclopropylacetylene, comprising the steps of
   (a) mixing between about 2.0 and about 2.5 equivalents of n-butyllithium in cyclohexane with one equivalent of 5-chloro-1-pentyne in cycyclohexane at about 0° C.;
   (b) heating the reaction to about 75° C. and maintaining the reaction at that temperature for about 5 hours, or until the cyclization is substantially complete;
   (c) cooling the reaction mixture to about 0° C.;
   (d) quenching the reaction with saturated $NH_4Cl$.

10. The process of claim 9, further comprising purifying the desired product cyclopropylacetylene.

* * * * *